(12) United States Patent
Grattan

(10) Patent No.: US 6,316,025 B1
(45) Date of Patent: Nov. 13, 2001

(54) SWALLOW TABLET COMPRISING PARACETAMOL

(75) Inventor: Timothy James Grattan, Guildford (GB)

(73) Assignee: SmithKline Beecham plc (GB)

(*) Notice: Subject to any disclaimer, the term of this patent is extended or adjusted under 35 U.S.C. 154(b) by 0 days.

(21) Appl. No.: 09/380,453

(22) PCT Filed: Feb. 27, 1998

(86) PCT No.: PCT/EP98/01284

§ 371 Date: Sep. 2, 1999

§ 102(e) Date: Sep. 2, 1999

(87) PCT Pub. No.: WO98/38983

PCT Pub. Date: Sep. 11, 1998

(30) Foreign Application Priority Data

Mar. 5, 1997 (GB) .................................. 9704524

(51) Int. Cl.⁷ .................................. A61K 9/20; A61K 9/48
(52) U.S. Cl. .................. 424/451; 424/452; 424/464; 424/465
(58) Field of Search .................. 424/464, 465, 424/451, 452, 489, 456, 453

(56) References Cited

U.S. PATENT DOCUMENTS

| 4,942,039 | * | 7/1990 | Duvall et al. | 424/466 |
| 5,348,745 | * | 9/1994 | Daher | 424/466 |

FOREIGN PATENT DOCUMENTS

| 195 02 789 A1 | 8/1996 | (DE) | A61K/31/13 |
| 0 377 906 A2 | 7/1990 | (EP) | A61K/9/46 |
| 0 418 564 A1 | 3/1991 | (EP) | A61K/9/46 |
| 2 103 087 A | 2/1983 | (GB) | A61K/33/06 |

\* cited by examiner

Primary Examiner—James M. Spear
(74) Attorney, Agent, or Firm—Dara L. Dinner; Stephen Venetianer; Charles M. Kinzig

(57) ABSTRACT

The present invention relates to a swallow tablet or capsule formulation comprising paracetamol, sodium bicarbonate, and at least one pharmaceutically acceptable excipient.

7 Claims, No Drawings

SWALLOW TABLET COMPRISING PARACETAMOL

This application is a 371 of PCT/EP98/01284 filed Feb. 27, 1998.

The present invention relates to pharmaceutical compositions containing N-acetyl-p-aminophenol, known by the generic names paracetamol, acetaminophen and APAP (hereinafter referred to as paracetamol). In particular, the invention relates to a fast acting paracetamol formulation in the form of a swallow tablet or capsule which has a greatly improved rate of absorption following ingestion by the patient.

Paracetamol is an analgesic and antipyretic agent which is widely used in prescription and non-prescription medicines, often in combination with other biologically active compounds. Following ingestion of paracetamol in a solid form, such as a tablet or capsule, the rate of absorption and hence the onset of pharmacological activity has been found to vary from patient to patient and can sometimes be very slow.

Many attempts have been made to improve the rate of onset of activity, for example by speeding up the disintegration of tablets by making effervescent formulations.

United Kingdom patent publication GB 2 103 087 (Bristol-Myers) describes an analgesic composition containing paracetamol that has an increased rate of absorption. GB 2 103 087 refers to a publication (J. Wojcicki et al, Zbl. Pharm., 118, (1979), Vol 2–3) describing investigations into the pharmacokinetics of paracetamol in which a single oral dose of 1000 mg of paracetamol was administered with 4000 mg of antacid in the form of calcium carbonate. According to the reference in GB 2 103 087, the combination was found to decrease the rate of absorption of paracetamol, when compared with the rate of absorption from paracetamol (1000 mg ) alone.

According to GB 2 103 087, an improved rate of absorption is achieved by co-administering a therapeutic dose comprising from about 150 mg to about 2000 mg of paracetamol with from about 60 mg to about 1200 mg of an antacid. The publication states that any antacid or combinations thereof commonly used to neutralise stomach acids may be used. GB 2 103 087 identifies antacids of special interest to be calcium carbonate, magnesium carbonate, a combination of calcium carbonate and magnesium carbonate, sodium bicarbonate and magnesium hydroxide. GB 2 103 087 exemplifies compositions comprising combinations of paracetamol with calcium carbonate, with a mixture of calcium carbonate and magnesium carbonate and with sodium bicarbonate.

The examples in GB 2 103 087 include two tablet formulations containing paracetamol and sodium bicarbonate; one such formulation comprises 325 mg of paracetamol and 225 mg of sodium bicarbonate wherein the weight ratio of sodium bicarbonate to paracetamol is 0.69 to 1, and the second formulation comprises 500 mg of paracetamol and 225 mg of sodium bicarbonate wherein the weight ratio of sodium bicarbonate to paracetamol is 0.4 to 1. When the various formulations exemplified in GB 2 103 087 were administered to healthy volunteers it was found that, for all the formulations tested, the actual increase in rate of absorption, was between 7 and 31% compared to conventional paracetamol tablets.

It has now been found unexpectedly that by selecting sodium bicarbonate and combining it with paracetamol in a tablet or capsule formulation such that it is present in an amount of at least 300 mg per tablet and the weight ratio of bicarbonate to paracetamol is at least 0.74 to 1, a swallow tablet or capsule can be produced which gives a statistically significant improvement in the rate of absorption over that obtained from a commercially available paracetamol tablet containing no sodium bicarbonate. This improvement is not observed when other antacids, eg. calcium carbonate, are combined with paracetamol in a solid dosage form at equivalent levels. More surprisingly, the rate of absorption following oral administration of such a solid dosage form comprising paracetamol and sodium bicarbonate also shows an improvement over that obtained following oral administration of an aqueous solution of a commercially available soluble product containing paracetamol and sodium bicarbonate. In the context of the present invention, an increase in the rate of absorption may be demonstrated as an increased in $C_{max}$, where $C_{max}$ is the maximum concentration of paracetamol in the serum, or by measuring the area under the concentration vs time curve in the first 20 minutes after dosing ($AUC_{0-20}$) when compared with other paracetamol compositions.

According to the present invention there is provided a swallow tablet or capsule formulation comprising from 300 mg to 600 mg of paracetamol and from 300 mg to 1200 mg of sodium bicarbonate wherein the weight ratio of sodium bicarbonate to paracetamol is at least 0.74 to 1.

For the avoidance of doubt, a swallow tablet is a tablet which is intended to be swallowed whole and not one which is intended for dissolution or suspension in water prior to administration, for example a tablet containing a substantial amount of an effervescent couple.

The tablet or capsule formulation of the invention preferably contains either 325 mg or 500 mg of paracetamol. The amount of sodium bicarbonate present in the formulation is favourably at least 370 mg, eg at least 400 mg or 500 mg and suitably is no greater than 1000 mg, preferably no greater than 800 mg and more preferably no greater than 700 mg. The weight ratio of sodium bicarbonate to paracetamol is favourably at least 0.8 to 1, preferably at least 1 to 1, and more preferably at least 1.25 to 1.

Formulations of the invention will generally contain at least one pharmaceutically acceptable excipient conventionally used in the art of tablet and/or capsule formulation. Suitable excipients which may be incorporated include lubricants, for example magnesium stearate and stearic acid; disintegrants, for example cellulose derivatives; starches; binders, for example modified starches and cellulose derivatives; glidants, for example colloidol silicas; compression aids, for example cellulose derivatives; as well as preservatives, suspending agents, wetting agents, flavouring agents, bulking agents, adhesives, colouring agents, sweetening agents appropriate to their form.

In addition to paracetamol, sodium bicarbonate and a pharmaceutically acceptable excipient, formulations of the invention may also contain other pharmaceutically active agents, for example other analgesics, anti-inflammatory analgesic agents, decongestants, antihistamines, antitussive agents, etc.. Formulations may also contain a pharmaceutically acceptable analgesic adjuvant, for example caffeine.

The invention also provides a process for the preparation of the tablet or capsule formulation of the invention, which process comprises the admixture of paracetamol and sodium bicarbonate together with any pharmaceutically acceptable excipients, additional pharmaceutically acceptable active agents or adjuvants. Thus the paracetamol and sodium bicarbonate may be mixed together with one or more binders and granulated using water. The resulting granule may then be dried, sieved and mixed with additional excipients such as a lubricant and disintegrant before being compressed into tablets. Alternatively, the sodium bicarbonate may be omitted from the granulation step and subsequently added with the other excipients. In an alternative process, tablets may be prepared using direct compression grades of paracetamol including commercially available forms which obviates the need for a granulation step. Tablets may also be prepared by other processes known in the art such as by shaping of an extruded mixture. For capsule production, the paracetamol and sodium bicarbonate may be mixed and granulated as for tablet production and filled into suitably sized capsule shells to the desired fill weight.

As stated above, the formulations according to the invention have an increased $C_{max}$, where $C_{max}$ is the maximum concentration of paracetamol in the serum, when compared with other paracetamol compositions. Comparative experiments have demonstrated an increased $C_{max}$ with respect to that obtained not only from swallow tablets containing only paracetamol or paracetamol plus calcium carbonate but also from proprietary soluble paracetamol formulations. Furthermore the formulations according to the invention have an increased ($AUC_{0-20}$), indicating an increased rate of absorption of paracetamol, when compared to conventional paracetamol swallow tablets.

Indeed, the plasma profile for the paracetamol formulations in accordance with the present invention is comparable to that expected to be achieved with a dose of paracetamol administered intravenously. (Seymore R. A., European J. Clin. Pharmacol., 20, 215–218, (1981), quotes 23.7 mg/liter in blood plasma following a 1000 mg iv dose of paracetamol.) Intravenous dosing of drugs is generally recommended in order to achieve a rapid maximum therapeutic effect which is not obtainable via oral dosing. However, intravenous dosing can be both painful and inconvenient. Moreover, since for a drug such as paracetamol which has poor solubility, intravenous formulations are not generally available, the present invention accordingly offers considerable practical benefit.

Furthermore, the addition of sodium bicarbonate in the weight ratio of the present invention has the potential added advantage that it may reduce the potential for patients to suffer toxic effects of paracetamol overdose, which can have fatal consequences or, at the very least, lead to irreversible liver damage. An intake of about 40 paracetamol tablets containing 500 mg paracetamol usually causes serious liver damage and sometimes proves fatal. The emetic dose of sodium bicarbonate is such that for most patients it would be achieved after swallowing tablets of the present invention well before the intake of paracetamol reaches a level that would prove fatal.

Another potential advantage of the formulations of the present invention is in the treatment of migraine. Proprietary products, for the alleviation of migraine headaches, which contain paracetamol also contain ingredients such as for example metaclopramide which is included to overcome the gastric stasis which accompanies migraine and promote gastric emptying in order to increase serum levels of paracetamol. Such ingredients can result in undesirable side effects. The formulations of the present invention which have an unexpectedly increased rate of absorption and thus obviate the need for additional ingredients carrying side effects, are clearly of benefit.

The following Examples (1 to 10) are illustrations of the invention. Comparative Example A is outside the scope of the invention but is included to further demonstrate the advantages of the invention.

EXAMPLE 1

A granule suitable for compression into tablets was prepared from the following ingredients

| ingredient | mg/tablet | batch size (g) |
| --- | --- | --- |
| 1. paracetamol (fine) | 500.00 | 9000.00 |
| 2. sodium bicarbonate (fine) | 630.00 | 11340.00 |
| 3. starch (maize) | 11.40 | 205.20 |
| 4. starch (pregelatinised) | 50.00 | 900.00 |
| 5. Povidone K25 | 2.00 | 36.00 |
| 6. potassium sorbate | 0.60 | 10.80 |

Ingredients 1–6 were sieved through a 16 mesh sieve into a suitable mixer and granulated with a suitable quantity of deionised water to form a medium/heavy granule. The granule was dried in a suitable oven at 45° C., until the water content was <1%. The resulting dried granule was then passed through a 12 mesh seive to give a white granule (yield 20.250 kg)

EXAMPLE 2

Tablets were prepared from the following ingredients:

| ingredient | mg/tablet | batch size (g) |
| --- | --- | --- |
| 1. granule from example 1 | 1194.00 | 19104.00 |
| 2. starch (maize) | 10.00 | 160.00 |
| 3. talc | 15.00 | 240.00 |
| 4. stearic acid | 5.00 | 80.00 |
| 5. Acdisol | 36.70 | 587.20 |
| Total | 1260.70 | 20171.20 |

Ingredients 1–5 were sieved through a 16 mesh sieve into a suitable blender and mixed. The resulting blend was then compressed into tablets using suitable capsule shaped tooling to give white capsule shaped tablets (target weight of 1260.7 mg), The final composition of the tablets was as follows:

| ingredient | mg/tablet |
| --- | --- |
| 1. paracetamol (fine) | 500.00 |
| 2. sodium bicarbonate (fine) | 630.00 |
| 3. starch (maize) | 21.40 |
| 4. starch (pregelatinised) | 50.00 |
| 5. Povidone K25 | 2.00 |
| 6. potassium sorbate | 0.60 |
| 7. talc | 15.00 |
| 8. stearic acid | 5.00 |
| 9. Acdisol | 36.70 |
| Total | 1260.70 |

Each tablet contained paracetamol 500 mg and sodium bicarbonate 630 mg, with a ratio of sodium bicarbonate:paracetamol of 1.26:1

EXAMPLE 3

Tablets (target weight 1023.82 mg) were prepared by a similar method to than described in examples 1 and 2, but using different levels of ingredients such that the final formula was as follows:

| ingredient | mg/tablet |
| --- | --- |
| 1. paracetamol (fine) | 500.00 |
| 2. sodium bicarbonate (fine) | 400.00 |
| 3. starch (maize) | 21.40 |
| 4. starch (pregelatinised) | 50.00 |
| 5. Povidone K25 | 2.00 |
| 6. potassium sorbate | 0.60 |
| 7. talc | 15.00 |
| 8. stearic acid | 5.00 |
| 9. Acdisol | 29.82 |
| Total | 1023.82 |

Each tablet contained paracetamol 500 mg and sodium bicarbonate 400 mg, with a ratio of sodium bicarbonate:paracetamol of 0.8:1

EXAMPLE 4

Tablets (target weight 993.82 mg) are prepared by a similar method to that described in examples 1 and 2, but using different levels of ingredients such that the final formula is as follows:

| ingredient | mg/tablet |
| --- | --- |
| 1. paracetamol (fine) | 500.00 |
| 2. sodium bicarbonate (fine) | 370.00 |
| 3. starch (maize) | 21.40 |
| 4. starch (pregelatinised) | 50.00 |
| 5. Povidone K25 | 2.00 |
| 6. potassium sorbate | 0.60 |
| 7. talc | 15.00 |
| 8. stearic acid | 5.00 |
| 9. Acdisol | 29.82 |
| Total | 993.82 |

Each tablet contains paracetamol 500 mg and sodium bicarbonate 370 mg, with a ratio of sodium bicarbonate:paracetamol of 0.74:1

EXAMPLE 5

Tablets (target weight 1430.7 mg) are prepared by a similar method to that described in examples1 and 2, but using different levels of ingredients such that the final formula is as follows:

| ingredient | mg/tablet |
| --- | --- |
| 1. paracetamol (fine) | 500.00 |
| 2. sodium bicarbonate (fine) | 800.00 |
| 3. starch (maize) | 21.40 |
| 4. starch (pregelatinised) | 50.00 |
| 5. Povidone K25 | 2.00 |
| 6. potassium sorbate | 0.60 |
| 7. talc | 15.00 |
| 8. stearic acid | 5.00 |
| 9. Acdisol | 36.70 |
| Total | 1430.70 |

Each tablet contains paracetamol 500 mg and sodium bicarbonate 800 mg, with a ratio of sodium bicarbonate:paracetamol of 1.6:1

EXAMPLE 6

Tablets (target weight 923.82 mg) are prepared by a similar method to that described in examples 1 and 2, but using different levels of ingredients such that the final formula is as follows:

| ingredient | mg/tablet |
| --- | --- |
| 1. paracetamol (fine) | 400.00 |
| 2. sodium bicarbonate (fine) | 400.00 |
| 3. starch (maize) | 21.40 |
| 4. starch (pregelatinised) | 50.00 |
| 5. Povidone K25 | 2.00 |
| 6. potassium sorbate | 0.60 |
| 7. talc | 15.00 |
| 8. stearic acid | 5.00 |
| 9. Acdisol | 29.82 |
| Total | 923.82 |

Each tablet contains paracetamol 400 mg and sodium bicarbonate 400 mg, with a ratio of sodium bicarbonate:paracetamol of 1:1

EXAMPLE 7

Tablets (target weight 1223.82 mg) are prepared by a similar method to that described in examples 1 and 2, but using different levels of ingredients such that the final formula is as follows:

| ingredient | mg/tablet |
| --- | --- |
| 1. paracetamol (fine) | 600.00 |
| 2. sodium bicarbonate (fine) | 500.00 |
| 3. starch (maize) | 21.40 |
| 4. starch (pregelatinised) | 50.00 |
| 5. Povidone K25 | 2.00 |
| 6. potassium sorbate | 0.60 |
| 7. talc | 15.00 |
| 8. stearic acid | 5.00 |
| 9. Acdisol | 29.82 |
| Total | 1223.82 |

Each tablet contains paracetamol 600 mg and sodium bicarbonate 500 mg, with a ratio of sodium bicarbonate:paracetamol of 0.83:1

EXAMPLE 8

Tablets (target weight 819.46 mg) are prepared by a similar method to that described in examples 1 and 2, but using different levels of ingredients such that the final formula is as follows:

| ingredient | mg/tablet |
| --- | --- |
| 1. paracetamol (fine) | 325.00 |
| 2. sodium bicarbonate (fine) | 409.50 |
| 3. starch (maize) | 13.91 |
| 4. starch (pregelatinised) | 32.50 |
| 5. Povidone K25 | 1.30 |
| 6. potassium sorbate | 0.39 |
| 7. talc | 9.75 |
| 8. stearic acid | 3.25 |
| 9. Acdisol | 23.86 |
| Total | 819.46 |

Each tablet contains paracetamol 325 mg and sodium bicarbonate 409.05 mg, with a ratio of sodium bicarbonate to paracetamol of 1.26:1

EXAMPLE 9

Tablets (target weight 1291.56 mg) are prepared by blending ingredients 1 to 7 together and compressing using a suitable tablet press:

| ingredient | mg/tablet |
| --- | --- |
| 1. paracetamol direct compression grade (90%) | 555.56 |
| 2. sodium bicarbonate | 630.00 |
| 3. microcrystalline cellulose | 50.00 |
| 4. Explotab (Na Starch Glycolate) | 25.00 |
| 5. Crosspovidone XL10 | 25.00 |
| 6. sodium lauryl sulfate | 3.00 |
| 7. magnesium stearate | 3.00 |
| Total | 1291.56 |

Each tablet contains paracetamol 500 mg and sodium bicarbonate 630 mg, with a ratio of sodium bicarbonate to paracetamol of 1.26:1

EXAMPLE 10

Capsules are prepared as follows:

The granulation, seiving and blending steps from examples 1 and 2 are repeated. The resulting powder is then filled into hard gelatin capsules with a target fill weight of 819.46 mg, such that the final formula is as follows:

| ingredient | mg/capsule |
| --- | --- |
| 1. paracetamol (fine) | 325.00 |
| 2. sodium bicarbonate (fine) | 409.50 |
| 3. starch (maize) | 13.91 |
| 4. starch (pregelatinised) | 32.50 |
| 5. Povidone K25 | 1.30 |
| 6. potassium sorbate | 0.39 |
| 7. talc | 9.75 |
| 8. stearic acid | 3.25 |
| 9. Acdisol | 23.86 |
| Total | 819.46 |

Each capsule contains paracetamol 325 mg and sodium bicarbonate 409.5 mg, with a ratio of sodium bicarbonate to paracetamol of 1.26:1

COMPARATIVE EXAMPLE A

Tablets (target weight 988.23 mg) were prepared by a similar method to that described in examples 1 and 2, but using different levels of ingredients and substituting calcium carbonate for sodium bicarbonate, such that the final formula was as follows:

| ingredient | mg/dose |
| --- | --- |
| 1. paracetamol (fine) | 500.00 |
| 2. calcium carbonate | 375.00 |
| 3. starch (maize) | 21.40 |
| 4. starch (pregelatinised) | 50.00 |
| 5. Povidone K25 | 2.00 |
| 6. potassium sorbate | 0.60 |
| 7. talc | 15.00 |
| 8. stearic acid | 5.00 |
| 9. Acdisol | 19.23 |
| Total | 988.23 |

Each tablet contained paracetamol 500 mg and calcium carbonate 375 mg, with ratio of calcium carbonate to paracetamol of 0.75:1

Biostudy

The following products were compared in a five way cross over pharmacokinetic study using 15 fasted healthy human volunteers:

| | |
| --- | --- |
| test formula A | Tablets from Example 2 |
| test formula B | Tablets from Example 3 |
| test formula C | Tablets from Comparative Example A |
| test formula D | Commercially available swallow tablets containing paracetamol (500 mg) and no sodium bicarbonate |
| test formula E | Commercially available soluble tablets containing paracetamol (500 mg) and sodium bicarbonate (1342 mg) |

Each volunteer swallowed 2 tablets of one of the formulations, followed by 100 mls of water on 5 separate occasions at least 48 hours apart. For test formula E, the 2 tablets were dissolved in the 100 mls of water prior to swallowing. Blood samples were taken at 5, 10, 15, 20, 25, 30, 35, 40, 45, 50, 60, 75, 90, 120, 180, 240, 360, 480, and 720 minutes post dose.

Serum paracetamol levels were determined by HPLC and paracetamol serum levels vs time profiles were plotted for each volunteer. There were no significant differences in the area under the serum level vs time curve ($AUC_{0-\infty}$) for any of the formulae.

The maximum concentrations of paracetamol in serum (Cmax) following dosing were as follows:

| | |
| --- | --- |
| test formula A | 30 mg/L |
| test formula B | 26 mg/L |
| test formula C | 15 mg/L |
| test formula D | 17 mg/L |
| test formula E | 20 mg/L |

The Cmax for formula A was statistically significantly higher than that seen for formula C ($p<0.0002$), D ($p<0.002$) and E ($p<0.02$). There was no statistically significant difference between the Cmax for formula A and B. The Cmax for formula B was significantly higher than that seen for formula C ($p<0.01$) and formula D ($p<0.02$)

The mean area under the serum concentration vs time curve between 0 and 20 minutes ($AUC_{0-20}$) following dosing were derived, results were as follows:

| | |
| --- | --- |
| test formula A | 245 mg.min/L |
| test formula B | 177 mg.min/L |

| test formula C | 76.0 mg.min/L |
| test formula D | 69.7 mg.min/L |
| test formula E | 199 mg.min/L |

The ($AUC_{0-20}$) for formulation A was 3.5 times greater than for formulation D and the ($AUC_{0-20}$) for formulation B was 2.5 times greater than for formulation D, both of these differences were statistically significant, indicating that the rate of paracetamol absorption from the invention was increased by a factor of up to 250% compared to conventional paracetamol swallow tablets.

What is claimed is:

1. A pharmaceutical formulation for a swallow tablet or capsule consisting essentially of from 300 mg to 600 mg of paracetamol and from 300 mg to 1200 mg of sodium bicarbonate together with at least one pharmaceutically acceptable excipient, wherein the weight ratio of sodium bicarbonate to paracetamol is at least 0.74 to 1.

2. A formulation according to claim 1 comprising at least 370 mg of sodium bicarbonate.

3. A formulation according to claim 1 comprising no greater than 1000 mg of sodium bicarbonate.

4. A formulation according to claim 1 containing 500 mg of paracetamol.

5. A formulation according to claim 1 containing 325 mg of paracetamol.

6. A formulation according to claim 1 wherein the weight ratio of sodium bicarbonate to paracetamol is at least 0.8 to 1.

7. A process for preparing a swallow tablet or capsule formulation according to claim 1 which process comprises the admixture of paracetamol and sodium bicarbonate together with the pharmaceutically acceptable excipient.

* * * * *